United States Patent
Elmarsafawi (10) Patent No.: US 8,531,189 B2
(45) Date of Patent: Sep. 10, 2013

(54) CEMENT EXPANSION MEASUREMENT APPARATUS AND METHOD

(75) Inventor: Youssef Elmarsafawi, Aberdeen (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 352 days.

(21) Appl. No.: 13/004,154

(22) Filed: Jan. 11, 2011

(65) Prior Publication Data

US 2011/0193564 A1 Aug. 11, 2011

(30) Foreign Application Priority Data

Feb. 8, 2010 (EP) .................................... 10290054

(51) Int. Cl.
*B29C 45/76* (2006.01)
*G01N 17/00* (2006.01)
*G01N 25/16* (2006.01)

(52) U.S. Cl.
USPC ............ 324/601; 264/40.1; 73/865.6; 374/56

(58) Field of Classification Search
USPC ......... 324/601; 264/40.1; 73/865.6; 374/56
See application file for complete search history.

(56) References Cited

U.S. PATENT DOCUMENTS

| | | |
|---|---|---|
| 3,779,085 A | 12/1973 | Rice |
| 4,197,753 A | 4/1980 | Harting et al. |
| 4,408,489 A | 10/1983 | Spangle |
| 5,487,307 A | 1/1996 | Landgren et al. |
| 6,817,238 B2 * | 11/2004 | Go Boncan et al. ............ 73/149 |
| 2003/0033893 A1 | 2/2003 | Go Boncan et al. |
| 2006/0117863 A1 | 6/2006 | Kim |

OTHER PUBLICATIONS

Nelson E.B. and Guillot D. (eds.): Well Cementing, 2nd Edition, Schlumberger, Houston (2006) 642, Fig. B21.
V.C. Goboncan, R.L. Dillenbeck, "Real-Time Cement Expansion/Shrinkage Testing Under Downhole Conditions for Enhanced Annular Isolation," Spe 79911.
S.S. Jennings, "Long-Term High-Temperature Laboratory Cement Data Aid in the Selection of Optimized Cements," Spe 95816.

* cited by examiner

*Primary Examiner* — Melissa Koval
*Assistant Examiner* — Farhana Hoque
(74) *Attorney, Agent, or Firm* — Michael Dae (57) ABSTRACT

An apparatus for measuring cement expansion comprises an expansion cell that comprises two nodes separated by a slit. The nodes are separated by a distance such that a change of the distance between the nodes may be correlated to a linear expansion of cement contained in the expansion cell. An electrical component is coupled to the two nodes, and the electrical component has an electrical property that may be correlated to the distance between the nodes. Measurement of the electrical-property change may be performed continuously and in real time. In addition, the expansion cell may be placed in a vessel equipped to simulate downhole pressure and temperature conditions.

20 Claims, 9 Drawing Sheets

CEMENT EXPANSION MEASUREMENT APPARATUS AND METHOD

RELATED APPLICATION INFORMATION

This patent application claims priority to European Patent Application Serial No. 10290054.5, filed on Feb. 8, 2010, and incorporated herein in its entirety.

BACKGROUND OF THE INVENTION

The statements in this section merely provide background information related to the present disclosure and may not constitute prior art.

Embodiments relate to an apparatus to measure expansion of cement. The cement expansion measuring apparatus may be used in oilfield related applications, for example, to measure the expansion of cement exposed to downhole conditions of pressure and temperature. Another embodiment relates to a cement expansion measurement method.

Cement is used for zonal isolation of a well that has been drilled in a geological formation for the purpose of hydrocarbon exploration and production. Such cements are exposed to harsh environments encountered downhole, typically fluid mixtures of hydrocarbon and water at high pressure 2.8 kilobars (40,000 psi) or high temperature up to 315° C. (600° F.). Developing new cement formulations requires measuring the expansion of cement when exposed to such downhole conditions of pressure and temperature.

U.S. Pat. No. 6,817,238 describes an apparatus for placement in a high-pressure, high-temperature (HPHT) chamber, and a method of measuring volumetric changes in set cement as the cement is exposed to pressures and temperatures similar to downhole conditions. The apparatus comprises a mold having a first section adjacent a base and a second section movably attached to the first section and adjacent the base in which cement may be placed. The apparatus includes a sensor to measure the movement of the first and second sections relative to one another in response to volumetric changes in the cement.

Despite the valuable contribution of U.S. Pat. No. 6,817,238 to the art, it has been observed that the mold has a relatively complex structure, rendering the cleaning for re-use after a cement slurry has set in the mold and volumetric changes in the cement has been measured relatively difficult. Further, simulating the geometrical condition of cement expanding in an annulus of a drilled wellbore would require a different shape. Furthermore, estimating linear expansion of the cement and/or measuring commonly certified (e.g. International Organization of Standards ISO, or American Society for Testing and Material ASTM, or American Petroleum Institute API) characteristics of the cement would also be valuable.

All of the above described references are incorporated herein in their entirety by reference thereto.

SUMMARY OF THE INVENTION

A cement expansion measuring apparatus and method that fulfill the needs observed herein are proposed.

In an aspect, embodiments relate to an apparatus to measure cement expansion.

In another aspect, embodiments relate to a method for measuring cement expansion or expansion of any other suitable settable composition such as for example geopolymers.

BRIEF DESCRIPTION OF THE DRAWINGS

The present invention is illustrated by way of examples and not limited to the accompanying drawings, in which like references indicate similar elements.

DETAILED DESCRIPTION

Figure 1:
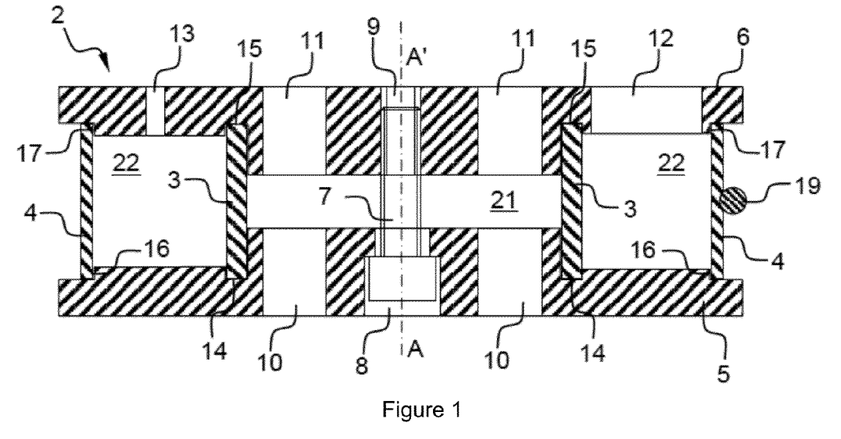
FIG. 1 is a side cross-sectional view of the expansion cell.

FIG. 1 is a cross-sectional view of the expansion cell 2 of a cement-expansion-measurement apparatus. The expansion cell 2 has a general cylindrical shape of revolution axis AA'. The expansion cell 2 comprises an inner ring 3, an outer expandable ring 4, a base plate 5 and a top plate 6. The different elements comprising the expansion cell are fastened together though a screw 7.

Figure 2:
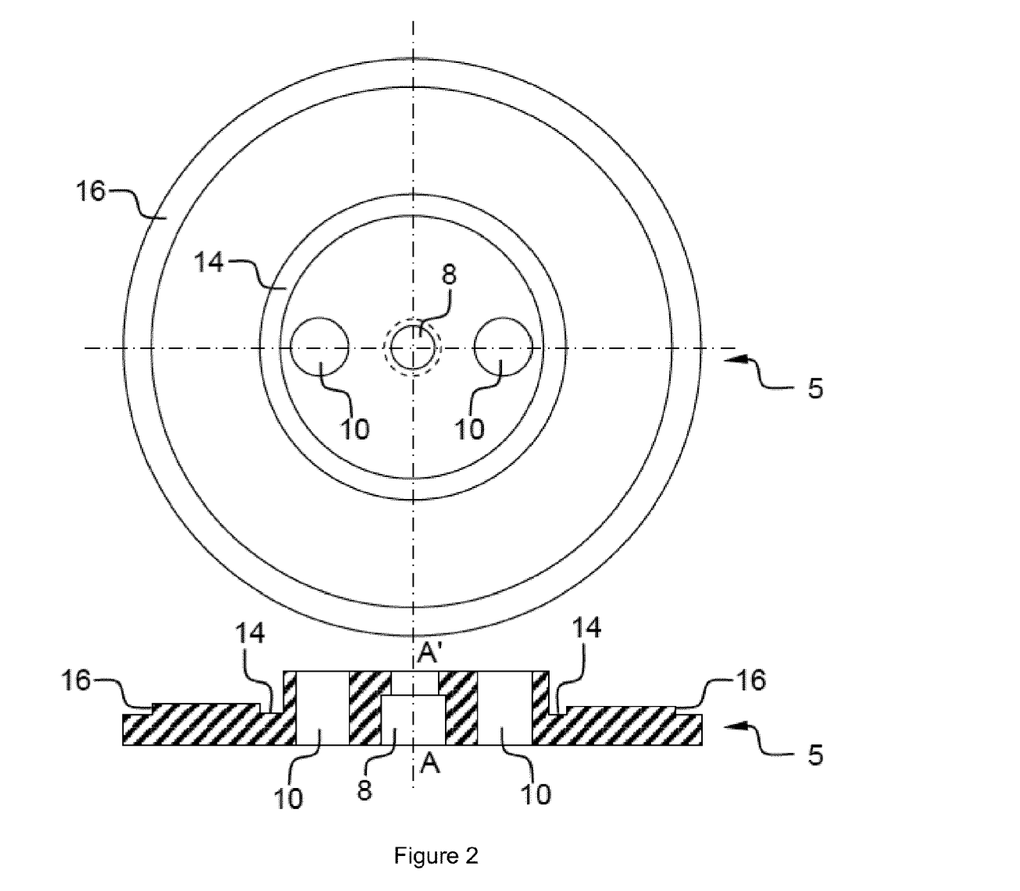
FIG. 2 presents top and side cross-sectional views of the base plate of the expansion cell.

The top portion of FIG. 2 illustrates the base plate 5. The bottom portion of FIG. 2 is a side cross-sectional view of the base plate 5. The base plate comprises a first bore 8 having a shoulder. An axis of the first bore may approximately correspond to the revolution axis AA'. The first bore 8 receives the screw 7 whose head is supported by the shoulder. The base plate 5 further comprises, in a central portion, two inlet bores 10 having respective axes deported from and parallel to the revolution axis AA'. The inlet bores 10 are positioned at a distance from the revolution axis AA' at a radius smaller than that of the inner ring 3. The base plate further comprises a base circular groove 14 receiving the lower portion of the inner ring 3. The base plate further comprises a base circular shoulder 16 receiving the lower portion of the outer expandable ring 4.

Figure 3:
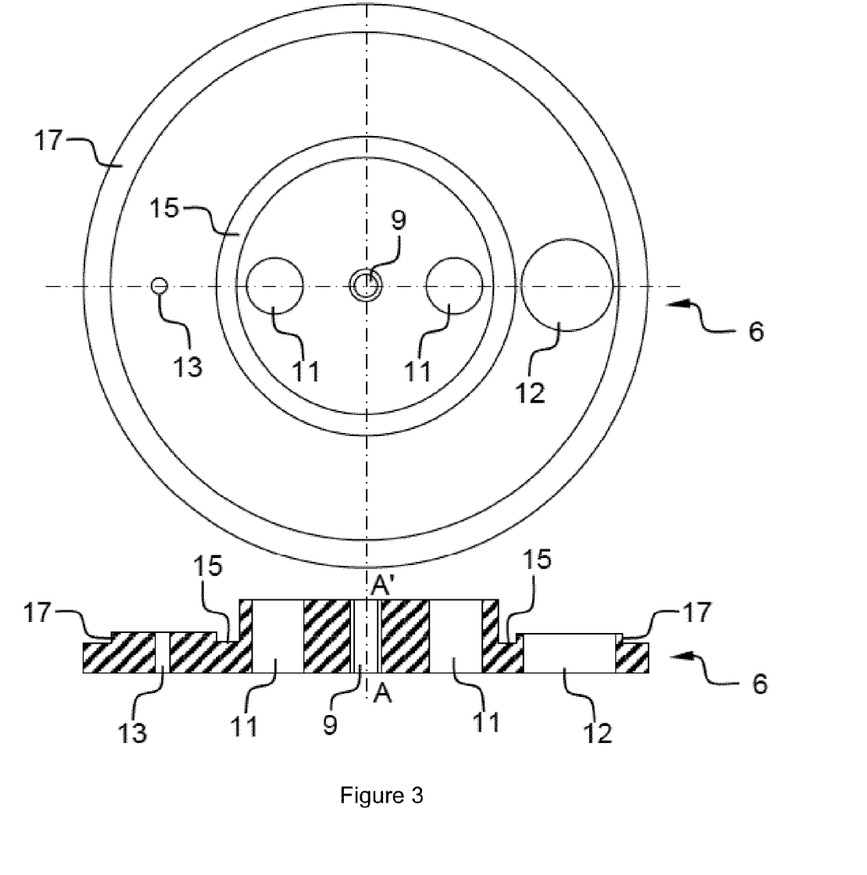
FIG. 3 presents top and side cross-sectional views of the top plate of the expansion cell.

The top portion of FIG. 3 top part illustrates the top plate 6. The bottom portion of FIG. 3 is a side cross-section view of the top plate 6. The top plate comprises a threaded bore 9. An axis of the threaded bore may approximately correspond to the revolution axis AA'. The threaded bore 9 receives the threaded portion of the screw 7. The top plate 5 further comprises, in a central portion, two outlet bores 11 having respective axis deported from and parallel to the revolution axis AA'. The outlet bores 11 are positioned at a distance from the revolution axis AA' that is smaller than the radius of the inner ring 3. The outlet bores 11 may approximately have the same symmetrical axis than the inlet bores 10 of the base plate 5. The outlet bores 11 allow the heated and pressurized fluid mixture to flow out through the top plate 6. The top plate further comprises a cement-injection bore 12 to inject a cement slurry into the annular space of the expansion cell 2. The top plate may further comprise an additional bore 13 of smaller diameter than the injecting bore 12 to facilitate expulsion of air contained in the expansion cell when the expansion cell 2 is filled in with a cement slurry. The top plate further comprises a top circular groove 15 receiving the upper portion of the inner ring 3. The top plate further comprises a top circular shoulder 17 receiving the upper portion of the outer expandable ring 4.

Figure 4A:
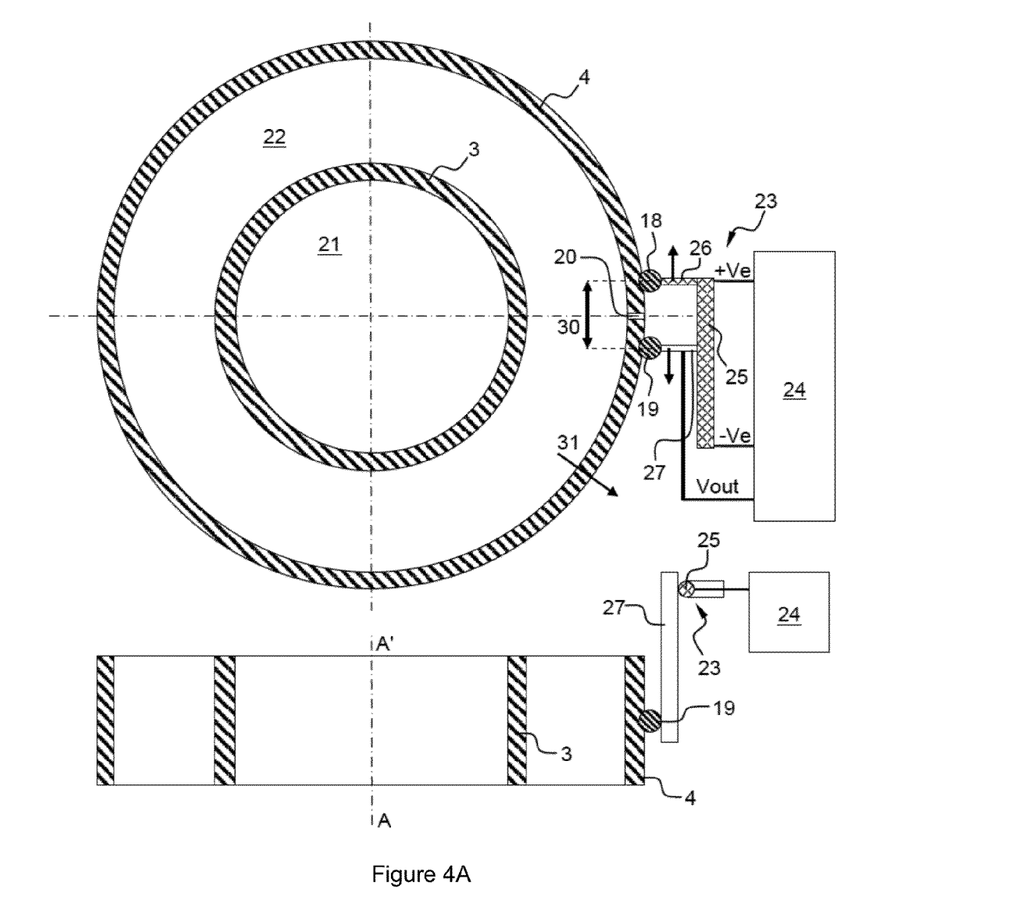
FIG. 4A presents top and cross-sectional views of an embodiment of an electrical component of the expansion cell.
Figure 4B:
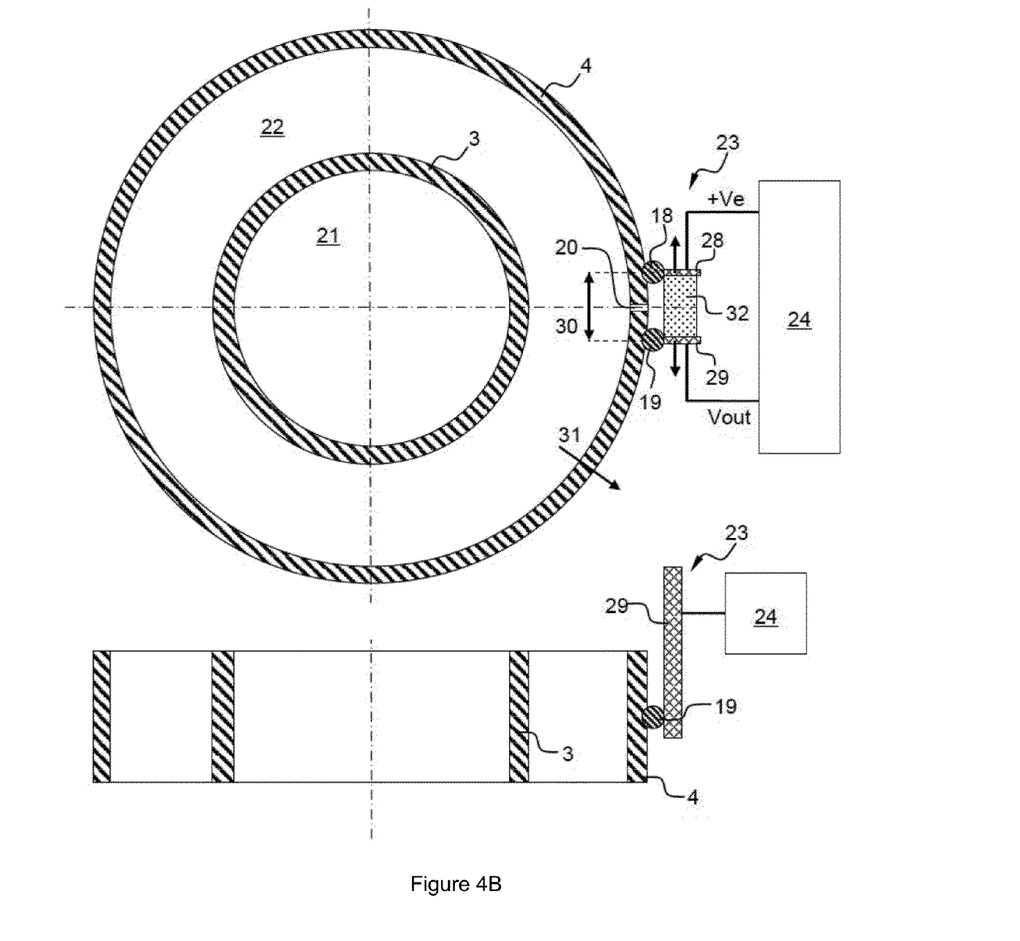
FIG. 4B presents top and cross-sectional views of another embodiment of an electrical component of the expansion cell.
Figure 7:
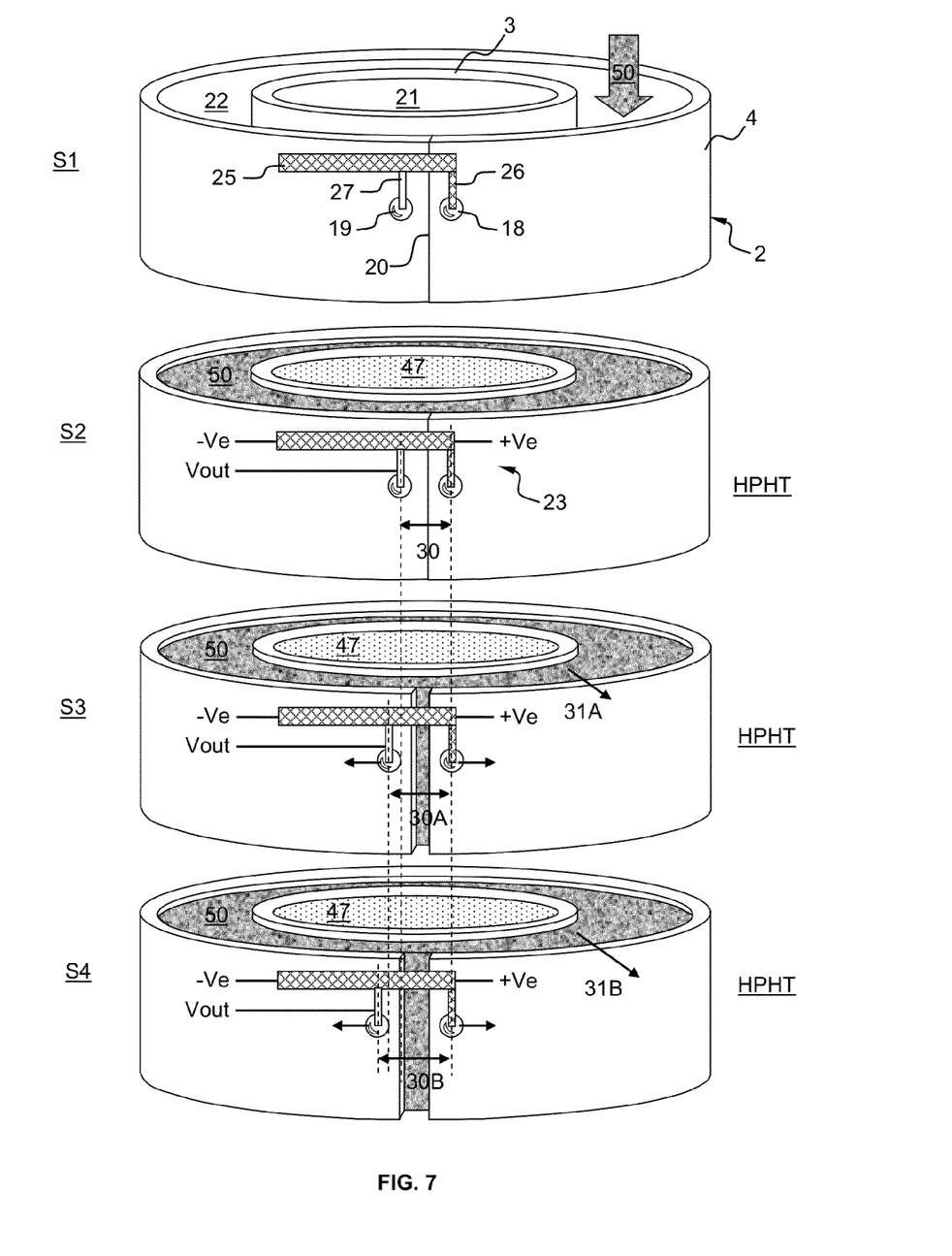
FIG. 7 presents a schematic diagram illustrating a cement expansion measuring method.

The outer expandable ring 4 has a larger diameter than a diameter of the inner ring 3. As shown in FIGS. 4 and 7, the outer expandable ring 4 comprises two nodes (18 and 19) separated by a slit 20. The slit 20 is substantially parallel to the revolution axis AA' of the expandable ring. The nodes (18 and 19) may be implemented as balls welded on the exterior wall of the outer ring 4. The nodes (18 and 19) are separated by a distance 30. Said distance 30 may be correlated to the linear expansion 31 of the cement contained in the expansion cell, as explained hereinafter in relation with FIG. 7.

Both the base circular groove 14 and the top circular groove 15 block in place the inner ring 3. Both the base circular shoulder 16 and the top circular shoulder 17 enable, on the one hand, blocking in place any movement of the outer expandable ring 4 towards the inner ring 3 and, on the other hand, allowing expansion of the outer expandable ring 4. When positioned between the base plate 5 and the top plate 6, the inner ring 3 and the outer expandable ring 4 define, on one hand, a first chamber 21 simulating a wellbore and, on the other hand, a second chamber 22 simulating an annulus of a wellbore, namely the space between the casing and the wellbore wall that needs to be filled with cement.

As depicted in FIG. 4, the expansion cell 2 is coupled to an electrical component 23 connected to a measuring arrangement 24. More precisely, the electrical component 23 is coupled to the two nodes (18 and 19) fixed to the outer expandable ring 4 and separated by the slit 20. The electrical component has an electrical property that is correlated to the distance 30 between the two nodes (18 and 19). When the cement expands in the expansion cell 2 according to a linear expansion 31, the distance 30 between the two nodes (18 and 19) changes, and thus the electrical property changes. Measuring the change of the electrical property allows one to estimate the distance 30 between the two nodes (18 and 19), and thus the cement linear expansion 31.

FIG. 4A shows top and side cross-sectional views of an embodiment of an electrical component 23 of the expansion cell. In this embodiment, the electrical property that is measured is resistance. One of the nodes 18 is fixedly coupled to a resistor 25, for example by a first connector 26. The other node 19 is movably coupled to the resistor 25, for example the node 19 is fixedly coupled to a wiper 27 sweeping the resistor 25 when the slit 20 opens. These elements form a potentiometer. In order to measure the resistance, one end of the resistor 25 fixedly coupled to one node 18 is connected to a voltage source +Ve, while the other end of the resistor 25 is connected to a voltage source −Ve. The voltage Vout at the wiper 27 is measured by the measuring arrangement 24. The connection to the voltage source/measuring arrangement can be made by means of wires and clips for ease of removal, however, any other removable connection may be satisfactory. The measuring arrangement 24 determines the resistance of the portion of resistor comprised between the connector 26 and the wiper 27 contacting points at the resistor 25. The resistance may then be related to the distance 30 between the two nodes (18 and 19) and to the linear expansion 31.

FIG. 4B shows top and side cross-sectional views of another embodiment of an electrical component 23 of the expansion cell. In this embodiment, the electrical property that is measured is capacitance. One of the nodes 18 is fixedly coupled to a first plate 28. The other node 19 is fixedly coupled to a second plate 29. As the plates are plunged in a non-conductive fluid mixture, a dielectric fluid layer 32 is formed between the first and second plates (28 and 29). These elements form a variable capacitor. In order to measure the capacitance, one plate 28 is connected to a voltage source +Ve. The voltage Vout at the other plate 29 is measured by the measuring arrangement 24. The connection to the voltage source/measuring arrangement can be made by means of wires and clips for ease of removal, however, any other removable connection may be satisfactory. The measuring arrangement 24 determines the capacity of the capacitor. The capacitance can then be related to the distance 30 between the two nodes (18 and 19) and to the linear expansion 31.

Figure 5:
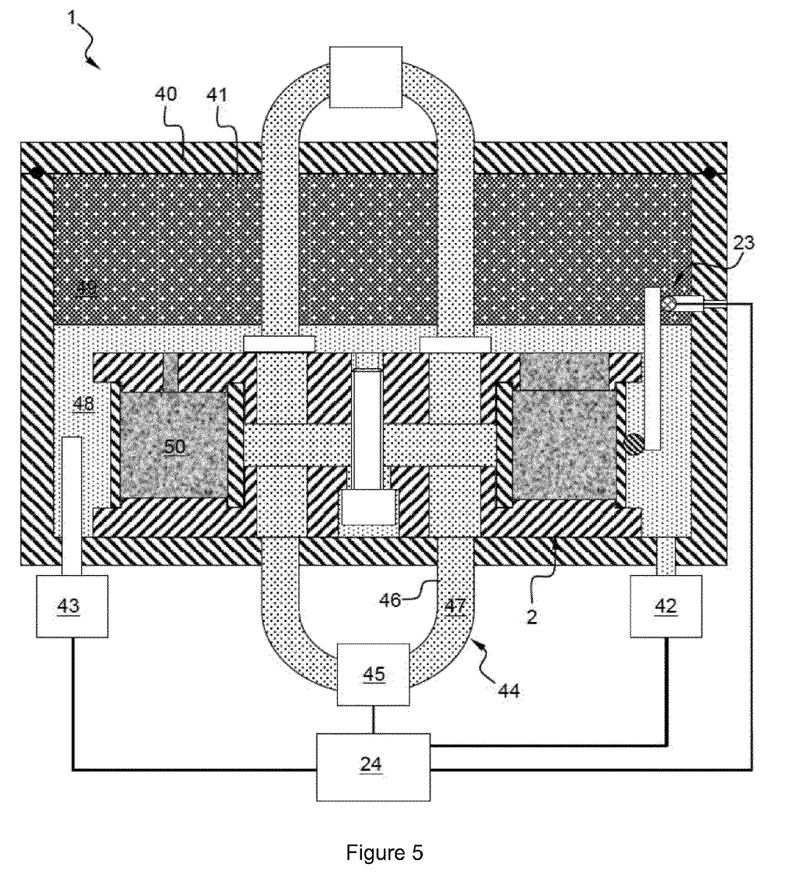
FIG. 5 presents a side cross-sectional view of an embodiment of a cement expansion measurement apparatus.

FIG. 5 is a side cross-sectional view of an embodiment of a cement expansion measuring apparatus 1. The cement expansion measuring apparatus 1 comprises a vessel 40 defining a high temperature, high pressure chamber 41. The vessel contains one expansion cell 2. The second chamber of the expansion cell 2 is filled in with cement 50. The vessel is coupled to a pump 42 and a heater 43 allowing exposure of the cement in the expansion cell 2 to simulated downhole pressure and temperature. The vessel is further coupled to a pump and heater arrangement 44. The pump and heater arrangement 44 comprises another pump and another heater 45, and a piping structure 46 for allowing flow of a fluid mixture 47 simulating inner wellbore conditions within the first chamber of the expansion cell 2. The pump 42, heater 43 and pumping and heater arrangement 44 may be coupled to the measuring arrangement 24 which may also control the downhole conditions to which the expansion cell 2 is exposed. The measuring arrangement may comprise a corresponding pumping controller and temperature controller (not shown). The high temperature, high pressure chamber 41 may be filled either by a conductive fluid 48 (e.g., water) and a non-conductive fluid 49 (e.g., oil), or only by a non-conductive fluid 49. As an alternative (not shown), the expansion cell 2 may be positioned into a sleeve filled in with a conductive fluid 48 (e.g., water). The electrical-component 23 parts connected to the voltage source are positioned within the layer of non-conductive fluid 49. In particular, the connector, the wiper or the plates can be extended above the layer of conductive fluid 48 when present.

Figure 6:
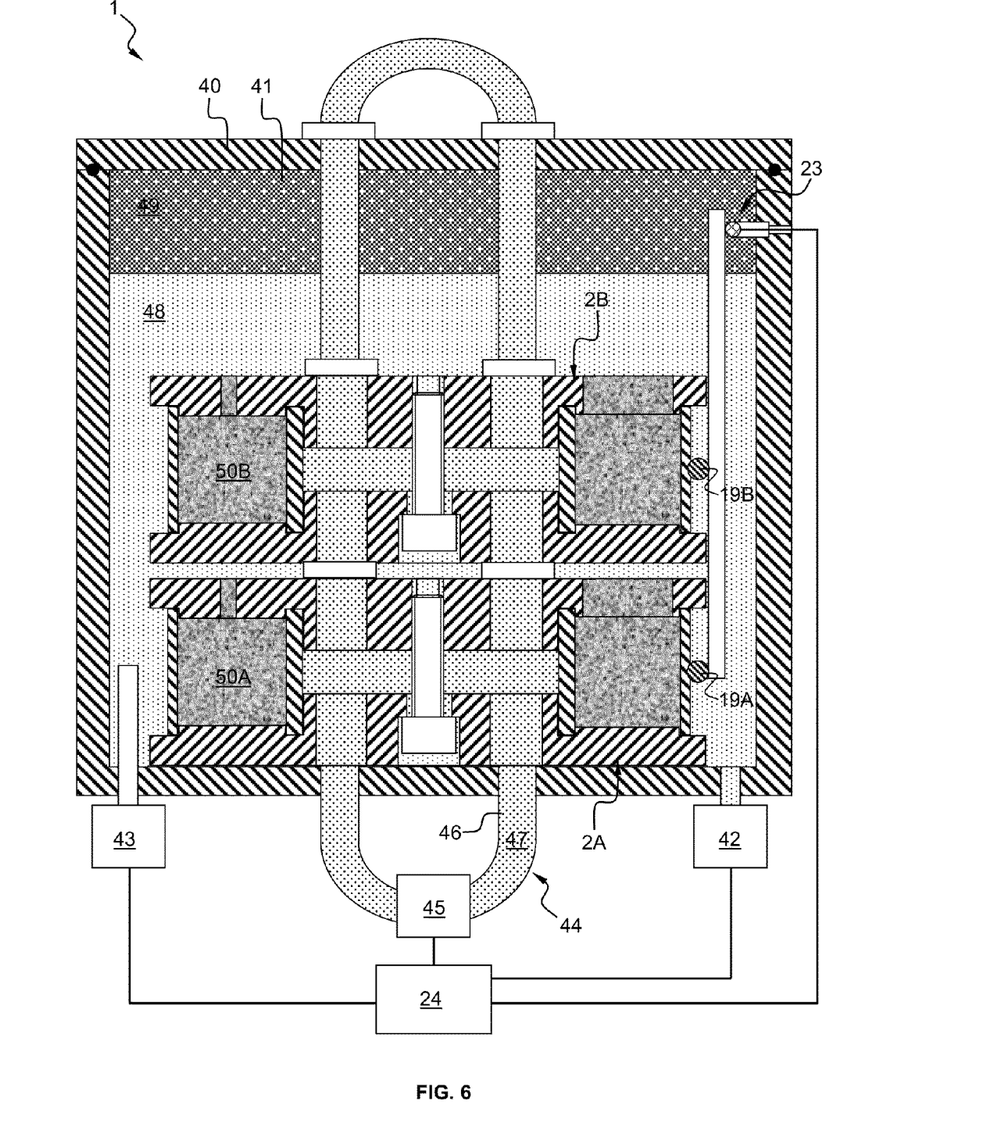
FIG. 6 presents a side cross-sectional view of another embodiment of a cement expansion measurement apparatus.

FIG. 6 is a side cross-sectional view of another embodiment of a cement expansion measuring apparatus. This embodiment differs from the embodiment of FIG. 5 in that a plurality, for example two expansion cells (2A and 2B) filled in with cements (50A and 50B) are disposed on each other in the vessel 40. Each expansion cell may be supported by a rack (not shown) in the vessel. FIG. 6 shows an embodiment in which the nodes (19A and 19B) of the respective expansion cells 2A and 2B are fixedly coupled to a single electrical component 23. Such an embodiment enables measuring the average linear expansion of both cements (50A and 50B).

Alternatively, according to another embodiment (not shown), each expansion cell 2A and 2B may be coupled to different electrical components. Such an embodiment enables measuring individually and independently the linear expansion of each cement 50A and 50B. In this particular embodiment, the chamber 41 of the vessel 40 is preferably filled in with a non-conductive fluid 49. Each electrical component may be connected separately to the measuring arrangement 24, or each electrical component may be multiplexed on a same wire connection.

FIG. 7 schematically illustrates a cement expansion measuring method. For sake of clarity, only some of the elements constituting the expansion cell and the vessel are shown.

In a first step S1, the connector 26, resistor 25 and wiper 27 are coupled to the nodes (18 and 19). The slit 20 is closed. The second chamber 22 of the expansion cell 2 is filled in with a cement slurry 50.

In a second step S2, the expansion cell 2 is positioned within the vessel. The electrical component 23 is coupled to the voltage source +Ve, −Ve of the measuring arrangement, and the output voltage Vout is also coupled to the measuring arrangement. From this starting point, the output voltage can be measured continuously. The vessel is closed and the measurement sequence begins while the expansion cell is exposed to the simulated downhole conditions HTHP. The slit 20 is still closed and the output voltage Vout corresponding to an initial distance 30 between the nodes (18 and 19) is measured. Advantageously, the fluid mixture 47 flows within the first chamber 21 defined by the inner ring 3 of the expansion cell 2 in order to simulate internal wellbore conditions.

In a third step S3, the cement begins to expand when exposed to the simulated downhole conditions HTPT and the slit 20 opens. The linear expansion 31A of the cement 50 is measured by determining the resistance between the two nodes (18 and 19) and estimating the distance 30A between the two nodes (18 and 19) and correlating said distance to the linear expansion 31A.

In a fourth step S4, at the end of the expansion process, the cement 50 no longer expands. The output voltage Vout corresponding to a final distance 30B between the nodes (18 and 19) is measured. The corresponding final linear expansion 31B can be estimated for characterizing the cement 50.

Figure 8:
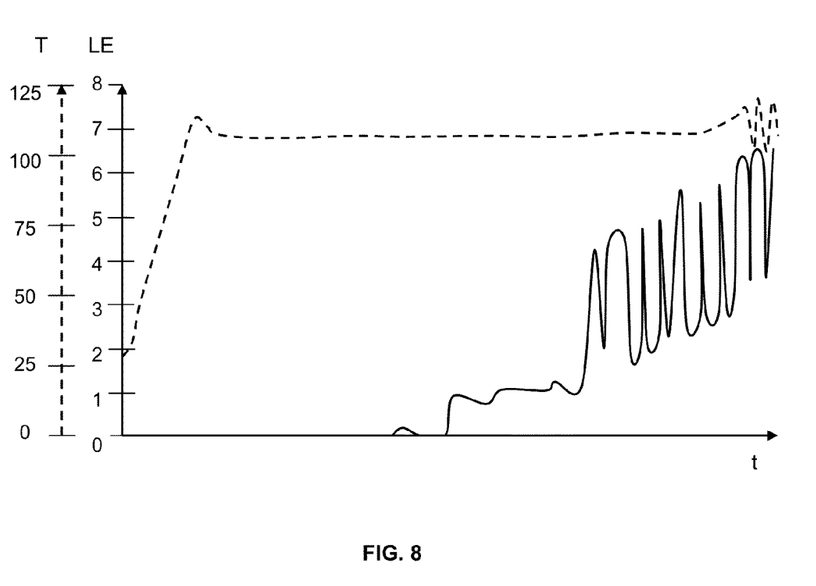
FIG. 8 presents a chart illustrating cement-expansion measurements.

FIG. 8 is chart illustrating such cement expansion measurements LE (full line) as a function of time t during the above-described steps. The evolution of the test temperature T (broken line) in Celsius degree as a function of time is also depicted on this chart.

Advantageously, before the hereinbefore-described measurement sequence takes place, a calibration of the expansion cell may be performed in order to determine the correspondence between the measured value (e.g. voltage) related to the electrical property and the distance between the two nodes when the slit is opening.

It should be appreciated that embodiments of the invention are not limited to the simulation of vertical wellbores as depicted on the drawings, said embodiments may also apply to the simulation of horizontal or deviated wellbores. The vessel can be adapted to contain more than two expansion cells. Although particular applications of the invention relate to the oilfield industry, other applications to other industries, for example, the mining industry, the water industry (water exploration and production) or the like also apply.

HTHP or HPHT when used in the present disclosure shall be understood as High-Temperature (up to for example 450° C.), High-Pressure (up to 3000 bars). However, measurement at ambient temperature and high pressure are also within the scope of the present invention. For example, the apparatus and method according to the present invention allow measurement of cement expansion above atmospheric pressure such as at 25° C. and of 70 bars of pressure.

The term "expansion" as used in the present document shall be understood as bulk expansion which is mainly seen as chemical expansion (e.g., hydration of MgO expanding agent). However, it is also within the scope of the present invention to measure thermal expansion of set cement blocks using same method with temperature cycling of the consistometer chamber.

It has to be noted that HTHP consistometers might be useful in the present invention. More detail about the general structure of the consistometer can be found in the following publication. "Petroleum and Natural Gas Industries—Cements and Materials for Well Cementing—Part 2: Testing of Well Cements," International Organization for Standards Publication No. 10426-2.

It may also be possible to measure expansion with different types of cells. An example is the one as disclosed in Nelson E. B. and Guillot D. (eds.): *Well Cementing, 2$^{nd}$ Edition*, Schlumberger, Houston (2006) 642, FIG. B21. However, for such a cell to adapted to work with the current method, the metal pins should be embedded in a cement slurry, the slurry would be allowed to set; then, the set cement could be placed in the equipment described herein and the measurement made between the pins.

The drawings and their description hereinbefore illustrate rather than limit the invention. Although a drawing shows different functional entities as different blocks, this by no means excludes implementations in which a single entity carries out several functions, or in which several entities carry out a single function. In this respect, the drawings are very diagrammatic. Any reference sign in a claim should not be construed as limiting the claim. The word "comprising" does not exclude the presence of other elements than those listed in a claim. The word "a" or "an" preceding an element does not exclude the presence of a plurality of such element.

The invention claimed is:

1. A cement-expansion-measurement apparatus, comprising:
   (i) an expansion cell comprising two nodes separated by a slit, such that a change of the distance between the nodes may be correlated to a linear expansion of cement contained in the expansion cell;
   (ii) an outer expandable ring comprising the slit, wherein the slit is substantially parallel to a revolution axis of the expandable ring;
   (iii) an inner ring with a diameter smaller than the that of the outer expandable ring, a first chamber defined by the inner ring, simulating a wellbore, and a second chamber between the inner ring and the outer expandable ring for containing cement, simulating an annulus of the wellbore;
   (iv) a base plate and a top plate, the base and top plate comprising at least one hole to allow a fluid mixture to flow within the first chamber, and the top plate comprising at least one hole for injecting a cement slurry in the second chamber;
   (v) an electrical component coupled to the two nodes, the electrical component having an electrical property correlated to the distance; and
   (vi) an arrangement for measuring the electrical property continuously and in real time, thereby estimating the linear cement expansion as the cement expands is exposed to simulated downhole conditions.

2. The apparatus of claim 1, further comprising a vessel that can accommodate at least one expansion cell, the vessel being further coupled to a pump and a heater, thereby allowing exposure of the cement in the expansion cell to simulated downhole pressure and temperature.

3. The apparatus of claim 1, wherein the electrical property is resistance, one of the nodes is fixedly coupled to a resistor, and the other node is movably coupled to the resistor, thereby forming a potentiometer.

4. The apparatus of claim 3, further comprising a vessel that can accommodate at least one expansion cell, the vessel being further coupled to a pump and a heater, thereby allowing exposure of the cement in the expansion cell to simulated downhole pressure and temperature.

5. The apparatus of claim 1, wherein the electrical property is capacitance, one of the nodes is fixedly coupled to a first plate, the other node is fixedly coupled to a second plate, and a nonconductive dielectric fluid layer is between the plates, thereby forming a variable capacitor.

6. The apparatus of claim 5, further comprising a vessel that can accommodate at least one expansion cell, the vessel being further coupled to a pump and a heater, thereby allowing exposure of cement in the expansion cell to simulated downhole pressure and temperature.

7. A method for measuring cement expansion comprising:
(i) filling an expansion cell with a cement, the expansion cell comprising:
   (a) two nodes separated by a slit, such that a change of the distance between the nodes may be correlated to a linear expansion of cement contained in the expansion cell;
   (b) an outer expandable ring comprising the slit, wherein the slit is substantially parallel to a revolution axis of the expandable ring;
   (c) an inner ring with a diameter smaller than the that of the outer expandable ring, a first chamber defined by the inner ring, simulating a wellbore, and a second chamber between the inner ring and the outer expandable ring for containing cement, simulating an annulus of the wellbore; and
   (d) a base plate and a top plate, the base and top plate comprising at least one hole to allow a fluid mixture to flow within the first chamber, and the top plate comprising at least one hole for injecting a cement slurry in the second chamber;
(ii) coupling an electrical component to the two nodes, the electrical component having an electrical property correlated to the distance; and
(iii) measuring the electrical property and estimating the linear cement expansion in a continuous, real-time manner.

8. The method of claim 7, further comprising placing the expansion cell in a vessel equipped to simulate downhole pressure and temperature.

9. The method of claim 7, further comprising allowing a fluid mixture to flow within a first chamber, the first chamber defined by an inner ring of the expansion cell.

10. The method of claim 7, further comprising a calibration step to determine a correlation between the electrical property and the distance between the two nodes.

11. The method of claim 7, wherein the electrical property is resistance.

12. The method of claim 11, further comprising placing the expansion cell in a vessel equipped to simulate downhole pressure and temperature.

13. The method of claim 11, further comprising allowing a fluid mixture to flow within a first chamber, the first chamber defined by an inner ring of the expansion cell.

14. The method of claim 11, further comprising a calibration step to determine a correlation between the resistance and the distance between the two nodes.

15. The method of claim 7, wherein the electrical property is capacitance.

16. The method of claim 15, further comprising placing the expansion cell in a vessel equipped to simulate downhole pressure and temperature.

17. The method of claim 15, further comprising allowing a fluid mixture to flow within a first chamber, the first chamber defined by an inner ring of the expansion cell.

18. The method of claim 15, wherein a nonconductive dielectric fluid is placed between the plates.

19. The method of claim 15, further comprising a calibration step to determine a correlation between the capacitance and the distance between the two nodes.

20. A method for measuring expansion comprising:
(i) filling an expansion cell with a settable composition, the expansion cell comprising:
   (a) two nodes separated by a slit, such that a change of the distance between the nodes may be correlated to a linear expansion of the settable composition contained in the expansion cell;
   (b) an outer expandable ring comprising the slit, wherein the slit is substantially parallel to a revolution axis of the expandable ring;
   (c) an inner ring with a diameter smaller than the that of the outer expandable ring, a first chamber defined by the inner ring, simulating a wellbore, and a second chamber between the inner ring and the outer expandable ring for containing the settable composition, simulating an annulus of the wellbore; and
   (d) a base plate and a top plate, the base and top plate comprising at least one hole to allow a fluid mixture to flow within the first chamber, and the top plate comprising at least one hole for injecting a settable composition slurry in the second chamber;
(ii) coupling an electrical component to the two nodes, the electrical component having an electrical property correlated to the distance; and
(iii) measuring the electrical property and estimating the linear expansion of the settable composition in a continuous, real-time manner.

* * * * *